United States Patent [19]
Blatt et al.

[11] Patent Number: 5,981,294
[45] Date of Patent: *Nov. 9, 1999

[54] DEVICE FOR BLOOD SEPARATION IN A DIAGNOSTIC DEVICE

[75] Inventors: Joel M. Blatt, Palo Alto; Wilma M. Mangan, Santa Clara; Paul J. Patel, Sunnyvale; Michael P. Allen, Los Altos, all of Calif.

[73] Assignee: Metrika, Inc., Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/564,441

[22] Filed: Nov. 29, 1995

[51] Int. Cl.$^6$ ....................................................... G01N 1/18
[52] U.S. Cl. .......................... 436/178; 436/531; 436/535; 422/73; 422/101; 210/482; 210/496; 435/7.1; 435/7.21; 435/7.24; 435/7.25
[58] Field of Search ..................... 422/73, 101; 436/178, 436/531, 535; 210/482, 496; 435/7.1, 7.21, 7.24, 7.25

[56] References Cited

U.S. PATENT DOCUMENTS

| | | | |
|---|---|---|---|
| 3,552,928 | 1/1971 | Fetter | 23/253 |
| 3,663,374 | 5/1972 | Moyer et al. | 195/103.5 R |
| 4,039,652 | 8/1977 | Adams et al. | 424/1 |
| 4,096,138 | 6/1978 | Scherr | 260/121 |
| 4,100,268 | 7/1978 | Scherr | 424/12 |
| 4,169,138 | 9/1979 | Jonsson | 424/12 |
| 4,181,636 | 1/1980 | Fisher | 260/8 |
| 4,210,723 | 7/1980 | Dorman et al. | 435/180 |
| 4,288,228 | 9/1981 | Oberhardt | 23/230 R |
| 4,301,412 | 11/1981 | Hill et al. | 324/442 |
| 4,419,453 | 12/1983 | Dorman et al. | 436/534 |
| 4,425,438 | 1/1984 | Bauman et al. | 436/527 |
| 4,477,575 | 10/1984 | Vogel et al. | 436/170 |
| 4,594,327 | 6/1986 | Zuk | 436/514 |
| 4,608,246 | 8/1986 | Bayer et al. | 424/11 |

(List continued on next page.)

FOREIGN PATENT DOCUMENTS

| | | | |
|---|---|---|---|
| 2019865 | 6/1990 | Canada | B01D 69/100 |
| 2020029 | 6/1990 | Canada | G01N 33/52 |
| 0217403 | 4/1987 | European Pat. Off. | G01N 33/52 |
| 0430395 | 6/1991 | European Pat. Off. | C12N 11/08 |
| 8501354 | 3/1985 | WIPO | G01N 33/54 |
| 9010869 | 9/1990 | WIPO | G01N 33/52 |
| 9114942 | 10/1991 | WIPO | G01N 31/22 |
| 9201226 | 1/1992 | WIPO | G01N 33/558 |
| 9201498 | 2/1992 | WIPO | G01N 33/92 |

OTHER PUBLICATIONS

A Dot–Immunobinding Assay for Monoclonal and Other Antibodies, Richard Hawkes, Evelyn Niday, and Julian Gordon, Analytical Biochemistry 119, pp. 142–147 (1982).

Detection of Specific Hybridoma Clones by Replica Immunoadsorption of their Secreted Antibodies, Jacqueline Sharon, Sherie L. Morrison, and Elvin A. Kabat, Dec. 7, 1978, Proc. Natl. Acad. Sci. USA vol. 76, No. 3, pp. 1420–1424 Mar. 1979.

Home Cholesterol Testing, Editorial, The Lancet, vol. 340, Dec. 5, 1992 No. 8832, p. 1386.

Reliability and Feasibility of Pregnancy Home–Use Tests: Laboratory Validation and Diagnostic Evaluation by 638 Volunteers, Joelle Daviaud, Dominique Fournet, Chantal Ballongue, Guy–Pierre Guillem, Alain LeBlanc, Claude Casellas, and Bernard Pau, Clin. Chem. 39/1, 53–59 (1993).

(List continued on next page.)

*Primary Examiner*—Randy Gulakowski
*Assistant Examiner*—Sharidan Carrillo
*Attorney, Agent, or Firm*—Timothy H. Gens; Trial & Technology Law Group

[57] ABSTRACT

The invention provides a filter for separating red blood cells from a whole blood sample to form plasma. The filter includes a solid phase support and an agglutinin for red blood cells. The agglutinin is insoluble in the whole blood sample and is immobilized on the solid phase support. The present invention also includes a device and method for determining the presence of at least one of a plurality of analytes in a sample of whole blood.

19 Claims, 2 Drawing Sheets

U.S. PATENT DOCUMENTS

| | | | |
|---|---|---|---|
| 4,627,445 | 12/1986 | Garcia et al. ............................ | 128/770 |
| 4,636,497 | 1/1987 | Martin et al. . | |
| 4,637,403 | 1/1987 | Garcia et al. ............................ | 128/770 |
| 4,637,978 | 1/1987 | Dappen .................................... | 435/11 |
| 4,744,760 | 5/1988 | Molday ...................................... | 424/3 |
| 4,753,776 | 6/1988 | Hillman et al. ......................... | 422/101 |
| 4,756,884 | 7/1988 | Hillman et al. ........................... | 423/73 |
| 4,787,398 | 11/1988 | Garcia et al. ............................ | 128/770 |
| 4,790,979 | 12/1988 | Terminiello ............................... | 422/56 |
| 4,816,224 | 3/1989 | Vogel et al. .............................. | 422/101 |
| 4,855,240 | 8/1989 | Rosenstein et al. .................... | 436/514 |
| 4,868,108 | 9/1989 | Bahar et al. .............................. | 436/535 |
| 4,883,764 | 11/1989 | Kloepfer .................................. | 436/178 |
| 4,935,147 | 6/1990 | Ullman et al. ........................... | 210/695 |
| 4,935,339 | 6/1990 | Zahradnik .................................. | 435/5 |
| 4,935,346 | 6/1990 | Phillips ..................................... | 435/14 |
| 4,987,085 | 1/1991 | Allen et al. ............................... | 436/169 |
| 5,037,645 | 8/1991 | Strahilevitz ............................. | 424/85.8 |
| 5,049,487 | 9/1991 | Phillips et al. .............................. | 435/4 |
| 5,059,394 | 10/1991 | Phillips .................................. | 422/68.1 |
| 5,064,541 | 11/1991 | Jeng et al. ............................... | 422/101 |
| 5,073,344 | 12/1991 | Smith et al. ............................. | 422/101 |
| 5,087,556 | 2/1992 | Ertinghausen ............................ | 435/7.9 |
| 5,110,724 | 5/1992 | Hewett .................................... | 435/11 |
| 5,114,350 | 5/1992 | Hewett .................................... | 435/288 |
| 5,114,859 | 5/1992 | Kagenow .................................. | 436/50 |
| 5,135,716 | 8/1992 | Thakore .................................... | 422/56 |
| 5,135,719 | 8/1992 | Hillman et al. ......................... | 422/101 |
| 5,139,685 | 8/1992 | de Castro et al. ....................... | 210/496 |
| 5,149,622 | 9/1992 | Brown ........................................ | 435/5 |
| 5,155,025 | 10/1992 | Allen et al. ............................... | 435/11 |
| 5,179,005 | 1/1993 | Phillips .................................... | 435/14 |
| 5,208,147 | 5/1993 | Kagenow et al. ......................... | 435/14 |
| 5,212,060 | 5/1993 | Maddox .................................... | 435/7.1 |
| 5,213,965 | 5/1993 | Jones ........................................ | 435/11 |
| 5,215,886 | 6/1993 | Patel ......................................... | 435/11 |
| 5,231,035 | 7/1993 | Akers, Jr. ................................. | 436/531 |
| 5,234,593 | 8/1993 | Kuroki et al. ............................ | 422/101 |
| 5,234,813 | 8/1993 | McGeehan et al. ..................... | 435/7.9 |
| 5,248,722 | 9/1993 | Siiman et al. ............................ | 536/112 |
| 5,262,067 | 11/1993 | Wilk et al. ................................ | 422/73 |
| 5,354,692 | 10/1994 | Yang et al. ............................. | 436/514 |
| 5,401,636 | 3/1995 | Craig ........................................ | 435/6 |
| 5,409,664 | 4/1995 | Allen ........................................ | 422/56 |
| 5,416,000 | 5/1995 | Allen et al. ............................... | 435/7.92 |
| 5,423,989 | 6/1995 | Allen et al. ............................... | 210/650 |
| 5,426,030 | 6/1995 | Rittersdorf et al. ...................... | 435/11 |
| 5,451,504 | 9/1995 | Fitzpatrick et al. ..................... | 436/531 |
| 5,458,852 | 10/1995 | Buechler .................................. | 422/102 |
| 5,552,064 | 9/1996 | Chachowski et al. ................... | 422/101 |
| 5,637,469 | 6/1997 | Wilding et al. ......................... | 435/7.21 |

OTHER PUBLICATIONS

Instrument–Free Quantitative Test Systems, MichaEl P. Allen and Prithipal Singh, Applications of Diagnostics, pp. 147–176 (1990).

DEVICE FOR BLOOD SEPARATION IN A DIAGNOSTIC DEVICE

RELATED APPLICATIONS

The subject matter of this application is related to a disposable single-use digital electronic instrument that is entirely self-contained, including all chemistry reagents, as disclosed in U.S. application Ser. No. 08/111,347 entitled "Novel Disposable Electronic Assay Device" filed Aug. 24, 1993 by Michael P. Allen, now abandoned, U.S. application Ser. No. 08/455,236 entitled "Novel Disposable Electronic Assay Device" filed May 31, 1995 by Michael P. Allen, now U.S. Pat. No. 5,580,794, and U.S. application Ser. No. 08/512,844 entitled "Dry Reagent Particle Assay And Device Having Multiple Test Zones And Method Therefor" filed Aug. 9, 1995 by Joel M. Blatt and Michael P. Allen. The above applications have the same assignee as the present invention and are incorporated herein by reference in their entirety.

FIELD OF THE INVENTION

The present invention relates to a method and device for separating plasma or serum from blood with sufficient speed and efficiency for immediate use in a diagnostic device.

BACKGROUND OF THE INVENTION

Many qualitative and quantitative diagnostic self-tests have developed in the clinical field utilizing blood as a sample. Although some of these techniques can be carried out on whole blood, it is necessary with many diagnostic assays to utilize serum or plasma separated from the blood sample to obtain an accurate analysis. Otherwise, the red blood cells or impurities in the blood sample could adversely affect a measurement of either reflected or transmitted light of a diagnostic test relying on either of these measurement techniques.

The most common conventional technique for separating plasma or serum from whole blood is by centrifugation. This technique, however, is time consuming and requires equipment that is not generally available outside of the clinical laboratory. For these reasons, centrifugation is entirely inappropriate for performing diagnostic self-tests by consumers or by professionals in point-of-care facilities.

A number of methods have been devised to avoid these problems. Usually a filtering device is used to separate red blood cells from plasma. Numerous materials have been used to form filters. Paper, fabric, glass or synthetic fibers, and membrane materials having a suitable pore size appear in the prior art.

For example, U.S. Pat. No. 4,816,224 to Vogel discloses a device for separating plasma or serum from whole blood and analyzing the serum using a glass fiber layer having specific dimensions and absorption to separate out the plasma from the whole blood for subsequent reaction. Among the problems of using glass fibers alone or in an admixture with other fibers is the slow rate of penetration by whole blood and the tendency to clog easily with practical yields of plasma usually being less than 25%. Furthermore, only small amounts of plasma or serum are entirely devoid of red blood cells or hemoglobin contamination which could interfere with subsequent quantitative measurements.

Another example is U.S. Pat. No. 4,753,776 to Hillman et al. which disclose a method of separating plasma from blood using a capillary force to drive the blood through fibers to a reaction area. Once the reaction area is saturated, the capillary force ceases and the transportation of the blood through the fibers and onto the reaction area stops. Two specific filtering media are disclosed: glass fibers alone or other cellulosic materials fibers using a soluble red cell agglutinin added in free form to the filtration medium. The free form of agglutinin, however, can migrate from the fibers to contaminate the plasma with the red blood cells bound to the agglutinin. Also, a portion of the plasma is unusable because it remains in the filter to fill the void volume created in the bed of fibers. Another problem can be the concentration of the agglutinin. A minimum amount of agglutinin is required to achieve agglutination. Too much agglutinin slows the movement of the plasma.

These prior art methods have proven unsuitable for applications involving diagnostic devices with space and volume restraints. Diagnostic devices also require an efficient method of separating plasma from a minute blood sample, often just one drop, to produce a sufficient volume of plasma to be transported through the assay portion of the device. The time allowed to complete the separation of the blood sample is also important so that the reaction chemistry can be accurately completed and the results are provided in a timely manner for the convenience of the user.

Thus, a need exists in the field of diagnostics for a blood separation filter and method which is sufficiently timely, efficient, and reliable for use in a diagnostic device which permits point-of-care use by untrained individuals in locations such as the home, sites of medical emergencies, or locations other than a clinic.

SUMMARY OF THE INVENTION

The present invention provides a filter for separating red blood cells from a whole blood sample to form plasma. The filter includes a solid phase support and an agglutinin for red blood cells. The agglutinin is insoluble in the whole blood sample and is immobilized on the solid phase support.

Preferably, one embodiment of the present invention provides a filter for separating red blood cells from a whole blood sample to form plasma wherein the filter includes a solid phase support made of a non-porous particle. The filter also includes an agglutinin for red blood cells. The agglutinin is insoluble in the whole blood sample and is immobilized on the solid phase support by being chemically bound directly to the solid phase support. The amount of agglutinin immobilized on the solid phase support provides about the same number of binding sites as the number of red blood cells in the sample of whole blood and at least 40% of the volume of the whole blood sample forms plasma. A second solid phase made of a porous material is immobilized within the second solid phase whereby the insoluble agglutinin immobilized on the solid phase support is also immobilized within the second solid phase.

The present invention also provides a filter for separating red blood cells from a whole blood sample to form plasma wherein the filter includes a housing defining an interior space. The housing has an inlet and an outlet to provide fluid communication between the interior space and the exterior of the housing. A solid phase support is immobilized within the interior space. The filter includes means for physically retaining the solid phase support within the flow path of the whole blood sample. An agglutinin for red blood cells, insoluble in the whole blood sample, is further immobilized on the solid phase support.

The present invention also includes a device for determining the presence of at least one of a plurality of analytes in a sample of whole blood. The device includes a housing having an exterior surface and a sample receptor means for receiving the sample of whole blood containing an analyte selected for determining its presence. The sample receptor means is located on the exterior surface of the housing. A filter receives the sample of whole blood from the sample receptor means. The filter has a solid phase support and an agglutinin for red blood cells. The agglutinin is insoluble in the whole blood sample and is immobilized within the solid phase support, whereby a sample of plasma is formed containing the selected analyte. A sample treatment means reacts the sample of plasma with a reagent to yield a physically detectable change which correlates with the amount of the selected analyte in the sample of plasma. The sample treatment means is within the housing and in fluid communication with the sample receptor means.

A method of determining the presence of one or more selected analytes in a sample of whole blood is provided by the present invention. The method includes the steps of introducing the sample of whole blood on the exterior surface of a container and filtering the sample of whole blood with a solid phase support and an agglutinin for red blood cells. The agglutinin is insoluble in the whole blood sample and is further immobilized on the solid phase support, whereby a sample of plasma is formed containing the selected analyte. The sample is transported to a reaction zone within the housing and chemically reacts the sample with at least one reagent to yield a physically detectable change which correlates with the amount of the corresponding selected analyte in the plasma sample.

Accordingly, it is an object of the present invention to provide a blood separation filter which efficiently separates red blood cells from a minute whole blood sample to yield sufficient plasma for transportation to and reaction with reagent chemistry within a diagnostic device.

It is a further object of the present invention to provide a blood separation filter which occupies a volume sufficiently small for use within a diagnostic device.

Another object of the present invention is to provide a filter and method for separating red blood cells from whole blood so that the reaction chemistry of a diagnostic device can be accurately completed and the results are provided in a timely manner for the convenience of the user.

Other and further advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

The present invention may be utilized in the disposable single-use digital electronic instrument and assay devices described in detail in the above-identified patent applications previously incorporated by reference. The present invention allows application of whole blood directly to these devices or to any other devices which rely upon the removal of red blood cells from a whole blood for an accurate analysis of the sample.

Generally, the present invention non-diffusively immobilizes an agglutinin upon a solid phase support which provides a zone in the path through which the whole blood sample flows. The agglutinin is insoluble within the whole blood sample and binds to the red blood cells. As a result, the red blood cells are indirectly immobilized upon the solid phase support and removed from the whole blood sample to yield a plasma or serum sample. The separation of the red blood cells from the whole blood sample is more efficient and timely completed than compared to the prior art and suitable for use in a wide variety of diagnostic devices.

The solid phase support can be any solid material to which an agglutinin can be immobilized and include, but are not intended to be limited to, beads, magnetic particles, paramagnetic particles, microparticles or macroparticles, test tubes, fabric or mesh that is woven or cast, and microtiter plates. Such solid phase support can be made from synthetic materials, naturally occurring materials, or naturally occurring materials which have been synthetically modified, and include, but are not intended to be limited to, cellulose materials, such as paper, cellulose and cellulose derivatives such as cellulose acetate and nitrocellulose, glass fibers, composite materials having synthetic material admixed with glass fibers, nitrocellulose, polyethylene, nylon, and polyester; fiberglass; naturally occurring cloth such as cotton; synthetic cloth such as nylon; porous gels, such as silica, agarose dextran, and gelatin; porous fibrous matrixes; starch based materials, such as cross-linked dextran chains; ceramic materials; olefin or thermoplastic materials including polyvinyl chloride, polyethylene, polyvinyl acetate, polyamide, polycarbonate, polystyrene, polyester, copolymers of vinyl acetate and vinyl chloride, combinations of polyvinyl chloride-silica; and the like.

The term agglutinin as used herein includes any chemical or biochemical agent capable of causing agglutination of red blood cells. The agglutinin must be insoluble within the whole blood sample so that it continues to be immobilized on the solid phase support. Agglutination is the formation of clumps or flocs of red blood cells due to the interaction of antigens on the cell surface with antibodies to form bridges linking the antigens. Agglutinins include, but are not limited to, antibodies to red blood cells and lectins. Immobilization can be conducted by chemically binding, adsorbing, absorbing, crosslinking or covalently attaching the agglutinin to the solid phase support. Preferably, the agglutinin is immobilized on the solid phase support using a mass ration of about 10:1.

The present invention can be used in assay devices having many configurations, some of which are specifically illustrated herein. Often these assay devices use a wicking member or transport matrix which is a porous material. By "porous" is meant that the material is one through which the test sample can easily pass and includes both bibulous and non-bibulous solid phase materials. In the present invention, the porous member can include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., polyethylene sheet material).

The assay devices include a sample receptor means for receiving a sample of whole blood containing at least one of a plurality of analytes selected for determining its presence. The sample receptor means is located on the exterior surface of the device housing and allows the whole blood sample to be applied to a sample pad, wicking material, transport matrix or the like. Subsequently, the red blood cells are removed from the whole blood sample to form a plasma sample.

The plasma sample is in fluid communication with a sample treatment means for chemically reacting the sample of plasma with at least one chemical reagent corresponding to an assay. Each reagent chemically reacts with the sample of plasma in a corresponding reaction zone located on the transport matrix to produce a reaction product mixture corresponding to each reagent. The sample treatment means also transports at least a portion of each reaction product mixture to a corresponding detection zone located on the transport matrix. The sample treatment means is located within the housing and is in fluid communication with the sample receptor means.

The present invention preferably uses particle detection for a detectable response or signal in each reaction zone related to the level of analyte in the sample. Other means for providing a detectable response in the reaction zones are suitable for use in the present invention. For example, and not for limitation, the analyte may be labeled with an indicator to measure electrical conductance or the reflectance or absorption of a characteristic light wavelength. As use herein, "indicator" is meant to include all compounds capable of labelling the analyte or conjugate thereof and generating a detectable response or signal indicative of the level of analyte in the sample.

Although the chemistry and configurations of the present invention may be used in an integrated assay device, the present invention can be used in any other instrumented reflectance or transmission meter as a replaceable reagent. Thus, the present invention also encompasses integrated assay instruments and analytical assay instruments comprising the present assay device.

A single channel test device 10 utilized in many of the experimental investigations described below is set forth in FIG. 1. The device 10 includes a sample pad 12 in fluid communication with a wick material 14. The wick material 14 transports the sample across its length. Similarly, an end pad 16 terminates the wick material 14 at the end opposite the sample pad 12. A sample containing whole blood is applied at the sample pad 12 and is separated into a plasma sample while the red blood cells are retained on the sample pad 12. The plasma sample passes through the wick material 14 and reaches the end pad 16.

Figure 2:
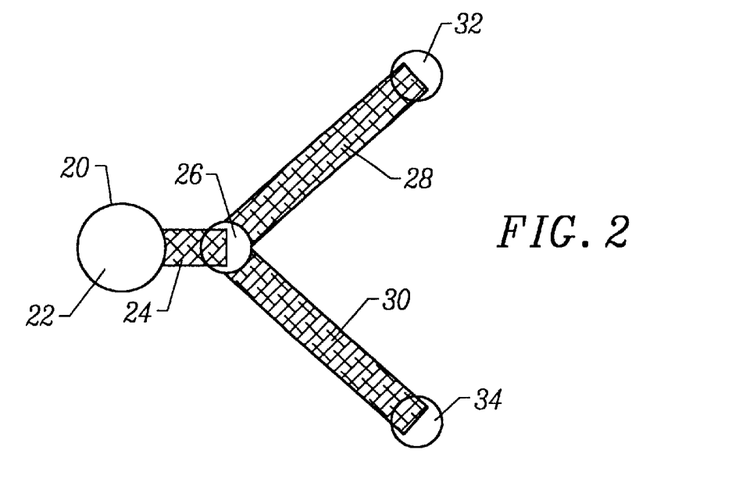
FIG. 2 is a top surface view of another diagnostic test device that can be used for simultaneous multiple quantitative and qualitative assays of plasma separated from a whole blood sample in accordance with the present invention.

Referring now to FIG. 2, a dual channel test device 20 utilized in the investigations described below is illustrated. The device 20 includes a sample pad 22 in fluid communication with a bridge 24 which connects to a distribution pad 26. Two separate wick materials 28 and 30 are in fluid communication at one end with the distribution pad 26 and at the opposite end with two reaction pads 32 and 36, respectively. A sample containing whole blood is applied at the sample pad 22 and is separated into a plasma sample while the red blood cells are retained in the sample pad 22. The plasma sample is transported by the bridge 24 and saturates the distribution pad 26. The plasma sample then proceeds simultaneously along the wick strips 28 and 30. The reaction pads 32 and 34 receive the plasma sample for reaction with chemical reagents deposited thereon to perform two diagnostic assays simultaneously.

Figure 3:
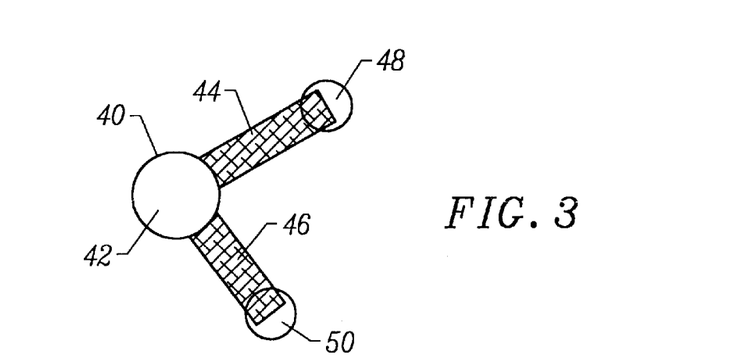
FIG. 3 is a top surface view of an embodiment of the present invention providing a diagnostic device for performing simultaneous multiple assays on plasma separated from a whole blood sample.

One of the preferred embodiments of the present invention is a diagnostic device 40 illustrated in FIG. 3 for performing multiple assays simultaneously. The device 40 includes a sample pad 42 for receiving a whole blood sample. The sample pad 42 includes a solid phase support which removes the red blood cells by binding them to an agglutinin immobilized on the solid phase support. Wicking strips 44 and 46 are in fluid connection with the sample pad 42 and transport the plasma sample to respective reaction pads 48 and 50 which contain the chemical reagents necessary for performing the diagnostic assays.

Figure 4:
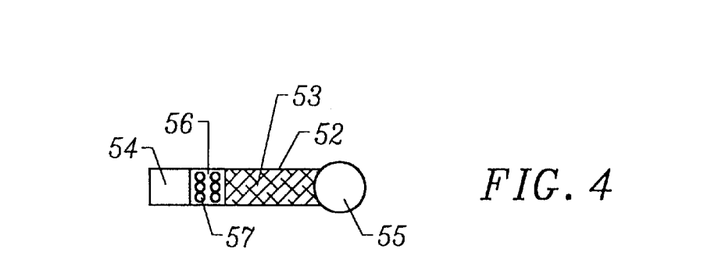
FIG. 4 is a top surface view of another embodiment of the present invention providing a diagnostic device for performing an assay on plasma separated from a whole blood sample.

Referring to FIG. 4, another preferred embodiment of the present invention is illustrated as a diagnostic device 52 for performing an assay. The device 52 includes a wicking strip 53 having a sample pad 54 at one end and a reaction pad 55 at the other end. After a sample containing whole blood is applied to the sample pad 54, the sample flows through a zone 56 containing a plurality of microparticles 57 having an agglutinin immobilized thereon. The microparticles 57 provide a solid phase support which binds to the agglutinin. In turn, the microparticles 57 themselves are immobilized within the zone 56. The zone 56 provides a second solid phase which physically retains the microparticles 57 therein. The second solid phase can be the same or different material which comprises the sample pad 54 or the wicking strip 53.

Alternately, the agglutinin can be immobilized directly on the material which comprises the zone 56 rather than on the microparticles 57. In this embodiment, the material which comprises the zone 56 provides the solid phase support. No second solid phase is used.

Figure 5:
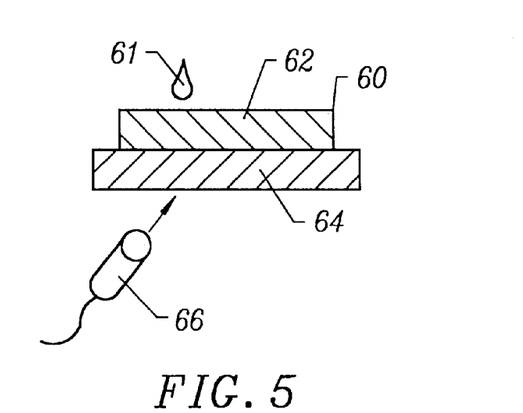
FIG. 5 is a cross-sectional side view of a sample pad and assay strip arranged in a stacked configuration for the separation of plasma from a whole blood sample in a diagnostic assay device.

FIG. 5 illustrates a stacked configuration for a diagnostic device 60 receiving a sample 61 containing whole blood. The device 60 includes a sample pad 62 which includes a solid phase support to remove the red blood cells by binding them to an agglutinin immobilized on the solid phase support. The resulting plasma flows to a reaction pad 64 which contains the chemical reagents necessary to perform the diagnostic assay and yield a physically detectable change. In this configuration, a detector 66 is positioned to view the physically detectable change in the area of the reaction pad 64.

Figure 6:
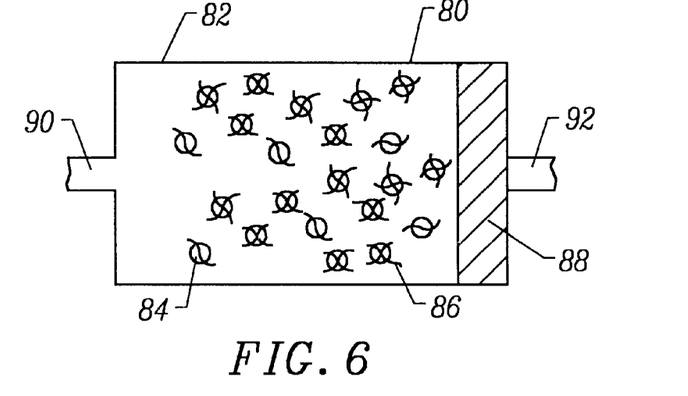
FIG. 6 is cross-sectional view of a container which houses a blood separation filter in accordance with the present invention.

The present invention also provides a filter 80 for separating red blood cells from a whole blood sample to form plasma as illustrated in FIG. 6. The filter 80 includes a container 82 which retains a solid phase support 84 in a zone within the flow path of a whole blood sample. Immobilized on the solid phase support is an agglutinin 86 suitable for binding to the red blood cells in the whole blood sample. The solid phase support 84 and immobilized agglutinin is retained within the container 82 by a membrane 88 wholly permeable to the whole blood or plasma sample. The membrane 88 physically entraps the solid phase support 84 within the container 82. The whole blood sample enters the container through inlet 90 and the plasma sample leaves through outlet 92.

Figure 7:
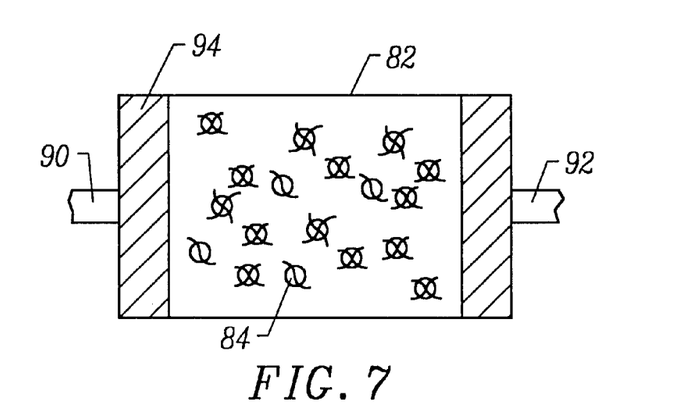
FIG. 7 is a cross-sectional view of an alternate embodiment of the blood separation filter in FIG. 6.

An alternate embodiment of the blood separation filter in FIG. 6 is illustrated in FIG. 7. The container 82 includes a second membrane 94 to retain the solid phase support 84 should the flow through the container be reversed. Reversing the flow through the container would be desirable, for example, to regenerate the binding capability of the agglutinin by removing the bound red blood cells. Any conventional method of cleaving the bond between the agglutinin and the red blood cell are suitable for use with the present invention. For example, the red cell binding function of the agglutinin can be regenerated by treating the solid phase support 84 with a solution having a high ionic strength, a low pH value, or a denaturing agent. Lysing the red blood cells with a surfactant is another suitable regeneration treatment.

The embodiments of FIGS. 6 and 7 are particularly useful for automated testing equipment or high volume applications. The regeneration feature of the present invention with either embodiment provides a widespread applicability with low cost and convenience.

EXAMPLE 1

Figure 1:
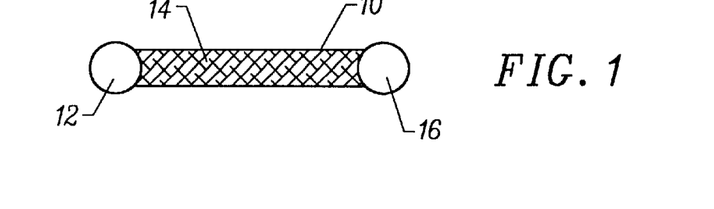
FIG. 1 is a top surface view of a diagnostic test device that can be used for quantitative and qualitative assays of plasma separated from a whole blood sample in accordance with the present invention.

To evaluate the effectiveness of various materials for their ability to wick whole blood, the sample pad 12 for device 10 in FIG. 1 was made of GF/D filter paper cut into a ¼ inch diameter disk. The various materials were cut into a 3 cm×0.2 cm size for use as the wick material 14. The end pad 16 was made of nitrocellulose cut into a ¼-inch disk. The nitrocellulose material was obtained from S&S catalog number AE 99 having an average pore size of 8 microns.

The tests were performed by applying 20 ul of whole blood. In each of the following tests unless otherwise noted, the whole blood used was obtained from Becton Dickinson as Vacutainer Cat. 367673 Lot 45852 which contains sodium heparin.

The results of these tests demonstrated that at least two materials could saturate the nitrocellulose end pad 16 in less than 3 minutes. One was a polyester woven screen material made by Tetko, Inc. under catalog number 7-2F777 D. The Tetko® material had a thickness of 205 um, weight of 4.01 oz/yd, and an air flow of 70 cfm/sq ft. Another suitable material was Porex catalog number 4588 which is a polyethylene material.

EXAMPLE 2

To evaluate the effectiveness of various materials to transport plasma to the end pad 16, the device 10 in FIG. 1 was again utilized. The same procedure in Example 1 was employed unless otherwise noted. The resulting length of clear plasma along the length of the material under test was observed. The nitrocellulose material described above had an observed separation of 3 mm using 10 uL of whole blood.

One of the materials tested was Whatman GFA, which is a glass microfiber composition without binder made by Whatman Specialty Products, Inc. The Whatman GFA material had an observed separation of about 8 mm using 30 uL of whole blood. The GFA material has a weight of 53 g/m with a thickness of 260 um and a mean pore size of 1.9 um.

A group of materials made by Ahlstrom of Mt. Holly Springs, Pa. under the Cytosep® tradename were tested using 40 uL of whole blood to yield an observed separation of 7 mm, 5 mm, and 9 mm for the respective catalog numbers 1660, 1661, and 1662. The Cytosep® materials have a composition of synthetic fiber material admixed with glass fibers with the following thicknesses 1660:0.33 mm, 1661:0.18 mm, and 1662:0.64 mm and are disclosed in U.S. Pat. No. 5,186,843 of which the entire teaching is hereby incorporated by reference.

Another material tested was a polyester composition made by America Filtrona of Richmond, Va. having a thickness of 1.1 mm. Using 50 uL of whole blood, the observed separation was 3 mm.

A fibrous composite material made by Pall of Port Washington, N.Y. under the tradename Hemadyne® had an average thickness of about 8.0 mils. Using 20 uL of whole blood, the observed separation was 5 mm.

EXAMPLE 3

To evaluate the effectiveness of those materials that produced separation in a device which performs more than one assay simultaneously, the device 20 illustrated in FIG. 2 was utilized. The sample pad (SP) 22 was made of CytoSep® 1660 cut into a ¼ inch diameter disk. The bridge (B) 24 was cut in a strip 2 mm×5 mm and made of CytoSep® 1661. The distribution pad (DP) 26 was made of CytoSep® 1660 and cut into a ⅛-inch disk. The wicking strips (WS) 28 and 30 were cut 15 mm×1.5 mm and made of Tetko® 7-2F777BM. Each reaction pad (RP) 32 and 34 was made of nitrocellulose S&S AE99 cut into a ⅛-inch diameter disk. Using 20 uL of whole blood, the reaction pads 32 and 34 saturated completely within three minutes.

EXAMPLE 4

Tests were run using the device 20 described in Example 3 with various agglutinins passively adsorbed directly onto the material comprising the sample pad and acting as the solid phase support. The agglutinin was adsorbed by dipping the material in a solution containing the agglutinin and subsequent drying in an oven. For comparison, the same type of agglutinins were also immobilized on latex microparticles acting as the solid phase support. The latex microparticles themselves were physically retained within the sample pad material. The specific agglutinins were rabbit antibody to human red blood cells (a-hRBC), soy bean agglutinin (SBA), wheat germ agglutinin (WGA) or a mixture of these agglutinins. The RBC was obtained from Rockrand, Inc Cat. No. 209-4139, Lot 701. The SBA and WGA were obtained from Sigma as Cat. Nos. L9640 and L1395 and Lot Nos. 94H4012 and 63H4005, respectively. The microparticles were obtained from the Magsphere Co. A concentration of 1 mg/mL was used to treat the solid phase support. The agglutinins were directly deposited on the solid phase support. Alternately, the agglutinins were first deposited on a microparticle (M) latex bead having a diameter of 0.403 um. The conjugate formed between each agglutinin and the microparticle had a concentration of 0.125% (w/v). The agglutinins were conjugated to the microparticles by carbodimide coupling chemistry as described in *Anal. Biochem*, 185, 131 (1990) by Grabarek, Z. and Gergely, J.

The results of blood separation using the various agglutinins on CytoSep® 1660 and Whatman GFA are found in TABLES 1 and 2, respectively. An untreated solid phase support is used as a control. The individual microparticle:agglutinin conjugates are listed as M:X. The individual parts of device 20 are abbreviated under the heading Support. The key to the performance information presented therein is:

+++=heavy red blood cell (RBC) contamination (dark red)

++=moderate RBC contamination (light to moderate red)
+=trace RBC contamination
−=clean plasma (no red coloration visible) each RP is reported separately i.e. RP/RP

TABLE 1

CytoSep ® 1660

| Support | Control | SBA | WGA | SBA + WGA | a-hRBC | M:ahRBC | M:SBA |
|---|---|---|---|---|---|---|---|
| SP | +++ | ++++ | +++ | +++ | +++ | +++ | +++ |
| B | +++ | + | ++ | − | + | +++ | +++ |
| DP | +++ | − | − | − | − | ++ | +++ |
| WS | +++/+++ | −/− | −/− | −/− | −/− | −/− | −/+ |
| RP | +++/+++ | −/− | −/− | −/− | −/− | −/− | −/+ |
| time-sec | 180 | 175 | 185 | 170 | 150 | 138 | 160 |

TABLE 2

Whatman GFA

| Support | Control | SBA | WGA | SBA + WGA | a-hRBC | M:ahRBC | M:SBA |
|---|---|---|---|---|---|---|---|
| SP | +++ | ++++ | +++ | +++ | +++ | +++ | +++ |
| B | +++ | + | ++ | + | − | ++ | − |
| DP | + | − | − | − | − | − | − |
| WS | −/− | −/− | −/− | −/− | −/− | −/− | −/− |
| RP | −/− | −/− | −/− | −/− | −/− | −/− | −/− |
| time-sec | 145 | 170 | 175 | 160 | 173 | 145 | 140 |

TABLES 1 and 2 demonstrate a significant improvement in separating plasma from blood by using a mixture of SBA and WGA, as well as with a-hRBC either singly or in combination. The distribution pad as well the bridge portions of the device 20 were largely free of coloration with all three conditions. In surprising contrast to the prior art, immobilizing the antibody on microparticles not only increased the blood separation efficiency but also reduced time for the plasma sample to reach the reaction. The filtering capacity of the device 20 was not diminished by a clogging of the pores or spaces between the solid phase support. This effect was most pronounced with the Whatman GFA solid phase support which also demonstrated generally faster blood separation times compared to those obtained with the CytoSep® 1660.

It was observed that about 10 uL of plasma was formed with a starting sample of whole blood of about 20 uL. With that starting sample size, at least 8 uL of plasma was formed regardless of the immobilized agglutinin. The present invention forms about 40% to about 50% plasma from a whole blood sample.

It was also observed that substantially all of the plasma was removed from the sample pad (SP). By contrast, the prior art requires that a significant portion of the plasma be retained in the blood separation filter material in order to fill the void volume in the material bed. The present invention allows substantially all of the plasma to be drawn out of the solid phase support. This leads to a significantly greater amount of plasma being generated by the present invention compared to the prior art materials for equal starting volumes of a whole blood sample.

EXAMPLE 5

Using the Whatman GFA material as the-solid phase support in the device 20, additional tests were run with the preparation of the rabbit immunoglobulin G to human red blood cells (RIgG). The RIgG was adsorbed directly on the solid phase support or immobilized on 0.403 um diameter latex microparticles (M) which in turn were immobilized on the solid phase support. TABLE 3 provides the results using RIgG and TABLE 4 uses SBA as the agglutinin. The key to performance includes:

TABLE 3

Whatman GFA Solid Phase Support

| Support Treatment | Quantity ug/disc | Separation achieved | Completion Time (sec) |
|---|---|---|---|
| None | N/A | No | 170 |
| RIgG on M | 0.71 | Yes | 120 |
| RIgG on N | 0.89 | Yes | 246 |
| RIgG on M | 1.06 | Yes | 127 |
| RIgG on M | 1.77 | Yes | 200 |
| RIgG | 1 | No | 149 |
| RIgG | 2 | Yes | 178 |
| RIgG | 5 | No* | 220 |
| RIgG | 10 | Yes | 240 |
| RIgG | 20 | Yes | 160 |

TABLE 4

Whatman GFA Solid Phase Support

| Support Treatment | Quantity ug/disc | Separation achieved | Completion Time (sec) |
|---|---|---|---|
| None | N/A | No | 170 |
| SBA on M | 0.85 | No | 125 |
| SBA on M | 1.1 | No# | >300 |
| SBA on M | 1.28 | Yes | 130 |
| SBA on M | 2.13 | Yes | 130 |
| SBA | 1 | No# | >300 |
| SBA | 2 | No | 200 |
| SBA | 5 | Yes | 125 |
| SBA | 10 | No# | >300 |
| SBA | 20 | No# | >300 |

# = Incomplete saturation of the reactions pads - the sample beads on the sample pad upon application and slowly penetrates the pad.

EXAMPLE 6

Using the CytoSep 1660® material in the device 20, additional tests were run. Using the agglutinin directly adsorbed to the material as the solid phase support was compared to immobilizing the agglutinin onto latex microparticles (M) as the solid phase support. The agglutinin:microparticle conjugate is then immobilized on the material as the second solid phase. The agglutinins used were the rabbit immunoglobulin G to human red blood cells (RIgG) and the soybean agglutinin (SBA). The RIgG was immobilized on 0.403 um diameter latex microparticles which in turn were immobilized on the material. TABLE 5 provides the results using RIgG and TABLE 6 uses SBA as the agglutinin. The key to performance includes:

TABLE 5

CytoSep ® 1660 Solid Phase Support

| Support Treatment | Quantity ug/disc | Separation achieved | Completion Time (sec) |
|---|---|---|---|
| None | N/A | No | 198 |
| RIgG on M | 0.71 | No | 225 |
| RIgG on M | 0.89 | Yes | 125 |

TABLE 5-continued

Cytosep ® 1660 Solid Phase Support

| Support Treatment | Quantity ug/disc | Separation achieved | Completion Time (sec) |
|---|---|---|---|
| RIgG on M | 1.06 | Yes | 155 |
| RIgG on M | 1.77 | Yes | 140 |
| RIgG | 1 | No | 140 |
| RIgG | 2 | No | 105 |
| RIgG | 5 | Yes | 100 |
| RIgG | 10 | Yes | 170 |
| RIgG | 20 | Yes | 145 |

TABLE 6

Cytosep ® 1660 Solid Phase Support

| Support Treatment | Quantity ug/disc | Separation achieved | Completion Time (sec) |
|---|---|---|---|
| None | N/A | No | 198 |
| SBA on M | 0.85 | No | 300 |
| SBA on M | 1.1 | Yes/No | 286 |
| SBA on M | 1.28 | No* | >360 |
| SBA on M | 2.13 | No* | >300 |
| SBA | 1 | No | 168 |
| SBA | 2 | No | 116 |
| SBA | 5 | Yes/No | 170 |
| SBA | 10 | Yes | 170 |
| SBA | 20 | Yes | 145 |

* = Incomplete saturation of the reactions pads - the sample beads on the sample pad upon application and slowly penetrates the pad.

EXAMPLE 7

Using the procedures described in Example 3 and 4, the concentration level of the agglutinins SBA and a-hRBC directly immobilized on the solid phase support was progressively increased. The results for CytoSep 1660 as the material are provided in TABLES 7 and 8 for SBA and a-hRBC respectively. The results for Whatman GFA as the material are provided in TABLES 9 and 10 for SBA and a-hRBC respectively. The key to performance includes:

TABLE 7

Cytosep ® 1660 Solid Phase Support

| Part | Control | SBA Conc. (mg/ml) | | | | |
|---|---|---|---|---|---|---|
| | | 0.05 | 0.1 | 0.25 | 0.5 | 1.0 |
| SP | +++ | +++ | +++ | +++ | +++ | +++ |
| B | +++ | ++ | ++ | ++ | ++ | + |
| DP | +++ | ++ | + | + | + | + |
| WS | +/++ | +/+ | +/+ | +/− | −/− | −/− |
| RP | +/++ | +/+ | +/+ | +/− | −/− | −/− |
| Time-sec | 198 | 108 | 116 | 170 | 170 | 145 |

TABLE 8

Cytosep ® 1660 Solid Phase Support

| Part | Control | a-hRBC Conc. (mg/ml) | | | | |
|---|---|---|---|---|---|---|
| | | 0.05 | 0.1 | 0.25 | 0.5 | 1.0 |
| SP | +++ | +++ | +++ | +++ | +++ | +++ |
| B | +++ | +++ | +++ | +++ | ++ | ++ |
| DP | +++ | ++ | ++ | + | − | − |

TABLE 8-continued

Cytosep ® 1660 Solid Phase Support

| Part | Control | a-hRBC Conc. (mg/ml) | | | | |
|---|---|---|---|---|---|---|
| | | 0.05 | 0.1 | 0.25 | 0.5 | 1.0 |
| WS | +/++ | ++/++ | +/+ | −/− | −/− | −/− |
| RP | +/++ | +/+ | +/+ | −/− | −/− | −/− |
| Time-sec | 198 | 140 | 105 | 100 | 105 | 110 |

TABLE 9

Whatman GFA Solid Phase Support

| Part | Control | SBA Conc. (mg/ml) | | | | |
|---|---|---|---|---|---|---|
| | | 0.05 | 0.1 | 0.25 | 0.5 | 1.0 |
| SP | +++ | +++ | +++ | +++ | +++ | +++ |
| B | ++ | ++ | ++ | + | + | + |
| DP | ++ | ++ | ++ | + | + | + |
| WS | +/+ | +/+ | +/+ | −/− | −/− | −/+ |
| RP | +/+ | *** | +/+ | −/− | *** | *** |
| Time-sec | 170 | >300 | 200 | 125 | >300 | >300 |

*** = Incomplete saturation of the reaction pads.

TABLE 10

Whatman GFA Solid Phase Support

| Part | Control | a-hRBC Conc. (mg/ml) | | | | |
|---|---|---|---|---|---|---|
| | | 0.05 | 0.1 | 0.25 | 0.5 | 1.0 |
| SP | +++ | +++ | +++ | +++ | +++ | +++ |
| B | ++ | ++ | ++ | ++ | + | + |
| DP | ++ | + | + | ++ | + | + |
| WS | +/+ | +/+ | −/− | ++/+ | −/− | −/− |
| RP | +/+ | +/+ | −/− | ++/+ | −/− | −/− |
| Time-sec | 110 | 149 | 118 | 220 | 240 | 160 |

EXAMPLE 8

Using the procedures described in Example 3 and 4, the concentration level of the agglutinins a-hRBC and SBA directly immobilized on the latex microparticles and then indirectly immobilized on the solid phase support was progressively increased. The results for CytoSep 1660 as the solid phase support are provided in TABLES 11 and 12 for a-hRBC and SBA respectively. The results for Whatman GFA as the solid phase support are provided in TABLES 13 and 14 for a-hRBC and SBA respectively. The key to performance includes:

TABLE 11

Cytosep ® 1660 Solid Phase Support

| Part | M:a-hRBC Conc. (%) | | | |
|---|---|---|---|---|
| | 0.1 | 0.125 | 0.15 | 0.25 |
| SP | +++ | +++ | +++ | +++ |
| B | +++ | ++ | ++ | +++ |
| DP | + | − | + | + |
| WS | +/+ | −/− | +/− | −/− |
| RP | +/+ | −/− | −/− | −/− |
| Time-sec | 225 | 125 | 155 | 140 |

TABLE 12

Cytosep ® 1660 Solid Phase Support

| | M:SBA Conc. (%) | | | |
|---|---|---|---|---|
| Part | 0.1 | 0.125 | 0.15 | 0.25 |
| SP | +++ | +++ | +++ | +++ |
| B | +++ | +++ | +++ | +++ |
| DP | +++ | ++ | ++ | + |
| WS | ++/++ | +/− | +/+ | −/− |
| RP | ++/++ | +/− | *** | *** |
| Time-sec | >300 | 286 | >360 | >300 |

*** = Incomplete saturation of the reaction pads.

TABLE 13

Whatman GFA Solid Phase Support

| | M:a-hRBC Conc. (%) | | | | |
|---|---|---|---|---|---|
| Part | Control | 0.1 | 0.125 | 0.15 | 0.25 |
| SP | +++ | +++ | +++ | +++ | +++ |
| B | ++ | + | + | − | + |
| DP | ++ | + | + | − | − |
| WS | +/+ | −/− | −/− | −/− | −/− |
| RP | +/+ | −/− | −/− | −/− | −/− |
| Time-sec | 110 | 120 | 246 | 127 | 200 |

TABLE 14

Whatman GFA Solid Phase Support

| | M:SBA Conc. (%) | | | | |
|---|---|---|---|---|---|
| Part | Control | 0.1 | 0.125 | 0.15 | 0.25 |
| SP | +++ | +++ | +++ | +++ | +++ |
| B | ++ | + | ++ | ++ | − |
| DP | ++ | + | + | + | − |
| WS | +/+ | +/+ | −/− | −/− | −/− |
| RP | +/+ | +/+ | *** | −/− | −/− |
| Time-sec | 110 | 125 | >300 | 120 | 130 |

As demonstrated by comparing the results in Examples 7 and 8, there is at least about a 5 fold increase in efficiency as a result of immobilizing the agglutinin on the solid phase support. Even increasing the concentration of the agglutinin improved rather than diminished its effectiveness. This is a surprising result compared to specific contrary disclosure in the prior art.

Another significant difference is that the present invention requires less agglutinin to be more efficient. The prior art requires at least a minimum amount of agglutinin to achieve agglutination. The present invention needs only that amount of agglutinin to create sufficient binding sites in the filter for the expected sample size.

Numerous modifications and variations of the present invention are possible in light of the above teachings. It is therefore to be understood that within the scope of the appended claims, the invention may be practiced otherwise than as specifically described herein.

What is claimed is:

1. A filter for separating red blood cells from a whole blood sample to form plasma, the filter comprising:

a non-porous solid phase support particle;

a solid phase support matrix membrane; and an agglutinin for red blood cells, the agglutinin being insoluble in the whole blood sample, the agglutinin further being immobilized by adsorption on the solid phase support particle, the agglutinin being immobilized on the non-porous solid phase support particle using a mass ratio of about 10:1, the solid phase support particle being immobilized by physical entrapment within the solid phase support matrix membrane, the agglutinin binding to red blood cells to separate the red blood cells from the whole blood sample.

2. The filter of claim 1 wherein the solid phase matrix membrane is a porous material.

3. The filter of claim 2 wherein the non-porous solid phase support particle has a diameter of about 0.4 um.

4. The filter of claim 1 wherein the solid phase support particle and immobilized agglutinin is applied to the solid phase support matrix membrane in a concentration of about 0.1% to about 0.25% weight/volume.

5. The filter of claim 1 wherein the agglutinin is immobilized on the non-porous solid phase support particle using a mass ratio of about 10:1.

6. The filter of claim 1 wherein the filter further comprises means for physically retaining the solid phase support matrix membrane within a flow path of the whole blood sample.

7. The filter of claim 1 wherein the solid phase support matrix membrane is a woven material selected from the group consisting of cellulose, nitrocellulose, polyethylene, nylon, and polyester.

8. The filter of claim 1 wherein the agglutinin is selected from the group consisting of rabbit IgG antibody to human red blood cells, soybean agglutinin, wheatgerm agglutinin, and lectins.

9. The filter of claim 1 wherein the filter forms about 10 uL of plasma from about 20 uL of whole blood.

10. The filter of claim 9 wherein the plasma is formed in under three minutes.

11. The filter of claim 1 forms about 40% to about 50% of plasma by volume from a sample of whole blood.

12. The filter of claim 1 wherein the amount of agglutinin immobilized on the solid phase support particle within the solid phase support matrix membrane provides about the same number of binding sites as the number of red blood cells in the sample of whole blood.

13. A filter for separating red blood cells from a whole blood sample to form plasma, the filter comprising:

a solid phase support made of a non-porous particle;

an agglutinin for red blood cells, the agglutinin being insoluble in the whole blood sample, the agglutinin further being immobilized on the solid phase support by being chemically bound directly to the solid phase support, the agglutinin being immobilized on the non-porous solid phase support particle using a mass ratio of about 10:1, the amount of agglutinin immobilized on the solid phase support providing about the same number of binding sites as the number of red blood cells in the sample of whole blood and at least 40% of the volume of the whole blood sample forms plasma, the agglutinin binding to red blood cells to separate the red blood cells from the whole blood sample; and a solid phase matrix membrane made of a porous material, the non-porous particle being immobilized within the solid phase matrix membrane, the insoluble agglutinin immobilized on the solid phase support particle also being immobilized within the solid phase support matrix membrane.

14. A filter for separating red blood cells from a whole blood sample to form plasma, the filter comprising:

a housing defining an exterior and an interior space, the housing having an inlet and an outlet to provide fluid communication between the interior space and the exterior of the housing;

a solid phase support matrix membrane immobilized within the interior space;

means for physically retaining the solid phase support matrix membrane within a flow path of the whole blood sample; and an agglutinin for red blood cells, the agglutinin being insoluble in the whole blood sample, the agglutinin further being immobilized by adsorption on a solid phase support particle which is immobilized by physical entrapment within the solid phase support matrix membrane, the agglutinin binding to red blood cells to separate the red blood cells from the whole blood sample, the agglutinin is immobilized on the non-porous solid phase support particle using a mass ratio of about 10:1.

15. The filter of claim 14 wherein the solid phase support particle is a non-porous particle.

16. The filter of claim 14 wherein the filter forms about 10 uL of plasma from about 20 uL of whole blood.

17. The filter of claim 14 wherein the plasma is formed in under three minutes.

18. The filter of claim 14 forms about 40% to about 50% of plasma by volume from a sample of whole blood.

19. The filter of claim 14 wherein an amount of agglutinin immobilized on the solid phase support particle within the solid phase support matrix membrane provides about the same number of binding sites as the number of red blood cells in the sample of whole blood.

* * * * *